United States Patent
Yanagita et al.

(12) 
(10) Patent No.: US 6,322,248 B1
(45) Date of Patent: Nov. 27, 2001

(54) X-RAY IMPINGING POSITION ALIGNMENT METHOD AND X-RAY TOMOGRAPHIC IMAGING METHOD AND APPARATUS

(75) Inventors: Hirofumi Yanagita; Masatake Nukui, both of Tokyo (JP)

(73) Assignee: GE Yokogawa Medical Systems, Limited, Tokyo (JP)

( * ) Notice: Subject to any disclaimer, the term of this patent is extended or adjusted under 35 U.S.C. 154(b) by 0 days.

(21) Appl. No.: 09/476,520

(22) Filed: Jan. 3, 2000

(51) Int. Cl.[7] ........................................ A61B 6/08
(52) U.S. Cl. .................. 378/205; 378/4; 378/11; 378/19; 378/20; 378/205
(58) Field of Search .................. 378/4, 8, 9, 11, 378/15, 19, 20, 206, 205, 147, 150, 151

(56) References Cited

U.S. PATENT DOCUMENTS 5,550,886 * 8/1996 Dobbs et al. ........................... 378/19
6,185,275 * 2/2001 Toth et al. ............................... 378/4

FOREIGN PATENT DOCUMENTS

| 6169914 | 6/1994 | (JP) . |
| 7116157 | 5/1995 | (JP) . |
| 10-118058 | 5/1998 | (JP) . |
| 10-211199 | 8/1998 | (JP) . |

* cited by examiner

*Primary Examiner*—Robert H. Kim
*Assistant Examiner*—Courtney Thomas
(74) *Attorney, Agent, or Firm*—Moonray Kojima

(57) ABSTRACT

In order to make an X-ray impinging position coincide with a fixed position from the beginning of a scan, in scanning a subject to be examined by an X-ray emitting/detecting apparatus, an X-ray focus position is predicted based on the temperature of an X-ray tube 20 prior to beginning the scan and scan conditions intended to be currently used, and the position of a collimator 22 or an X-ray detector 24 is adjusted so that the X-ray impinges upon a fixed position on the X-ray detector 24.

6 Claims, 7 Drawing Sheets

| Condition | | Axial scan | | | | |
|---|---|---|---|---|---|---|
| | | 1 | 2 | 3 | 4 | 5 |
| Temperature of X-ray tube | (T) | <10% | ← | ← | ← | >90% |
| Tilt angle | (U) | -30° | +30° | ← | ← | ← |
| Scan time | (V) | 3 sec | ← | ← | 0.8 sec | ← |
| Focus size | (W) | small | ← | large | ← | ← |
| Collimator position | | Z1 | Z2 | Z3 | Z4 | Z5 |

| Condition | | Stationary scan | | | | |
|---|---|---|---|---|---|---|
| | | 1 | 2 | 3 | 4 | 5 |
| Temperature of X-ray tube | (T) | <10% | ← | ← | ← | >90% |
| Tilt angle | (U) | -30° | +30° | ← | ← | ← |
| Scan time | (X) | 0° | ← | ← | 180° | ← |
| Focus size | (W) | small | ← | large | ← | ← |
| Collimator position | | Z1 | Z2 | Z3 | Z4 | Z5 |

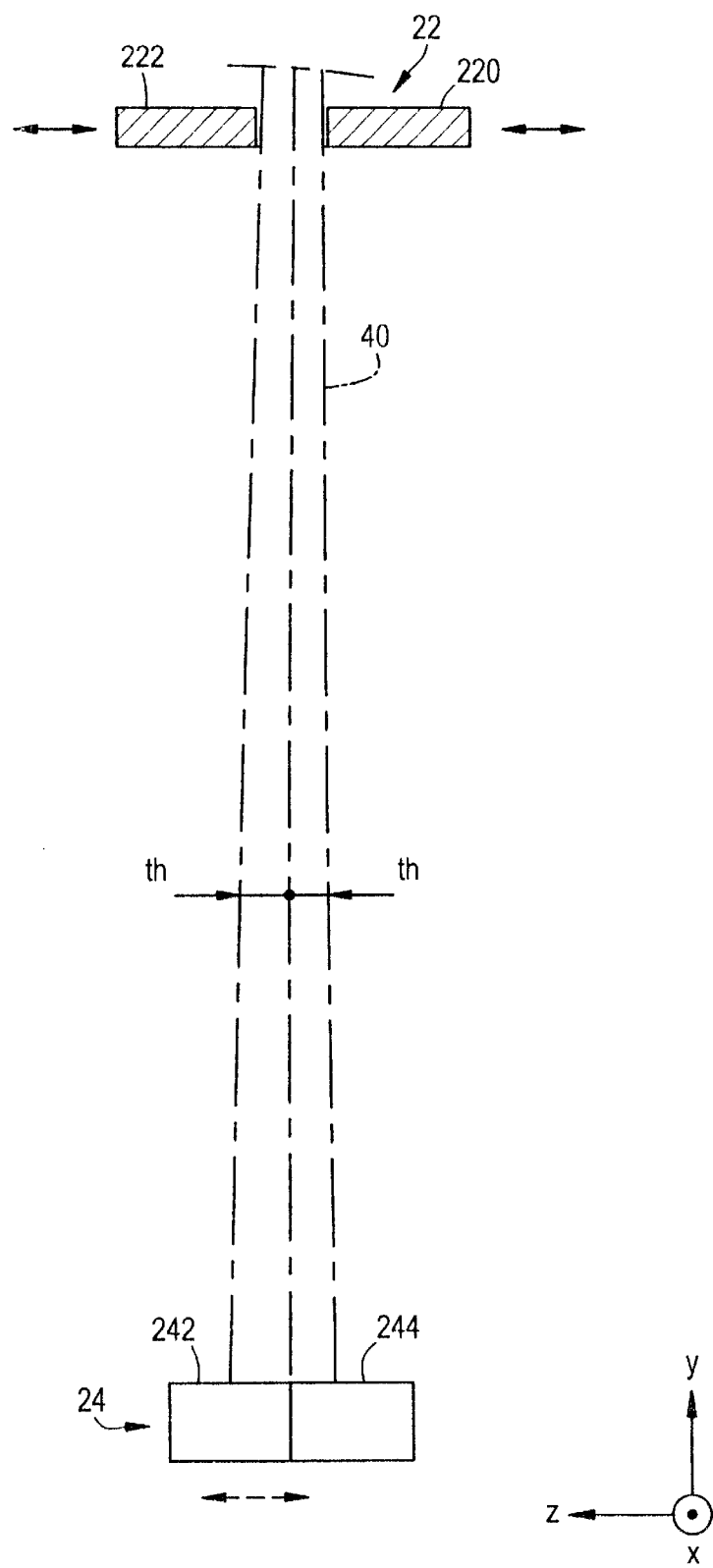

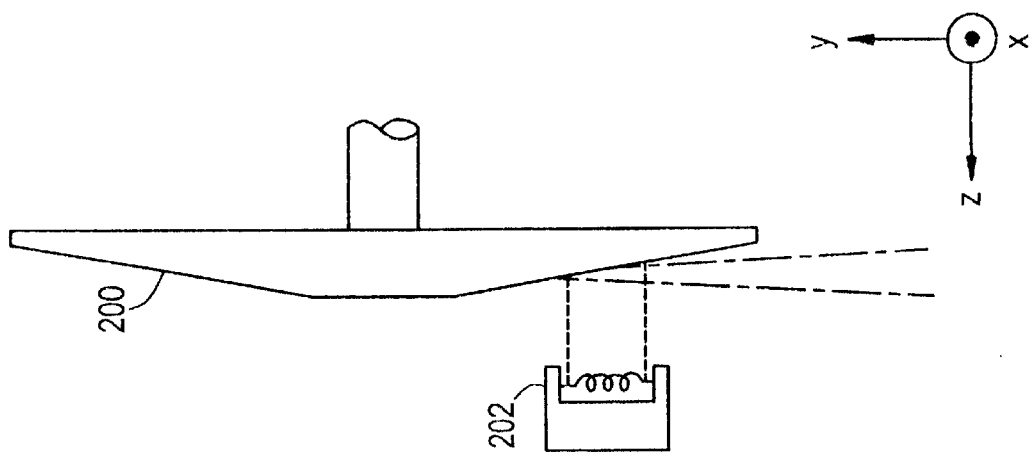
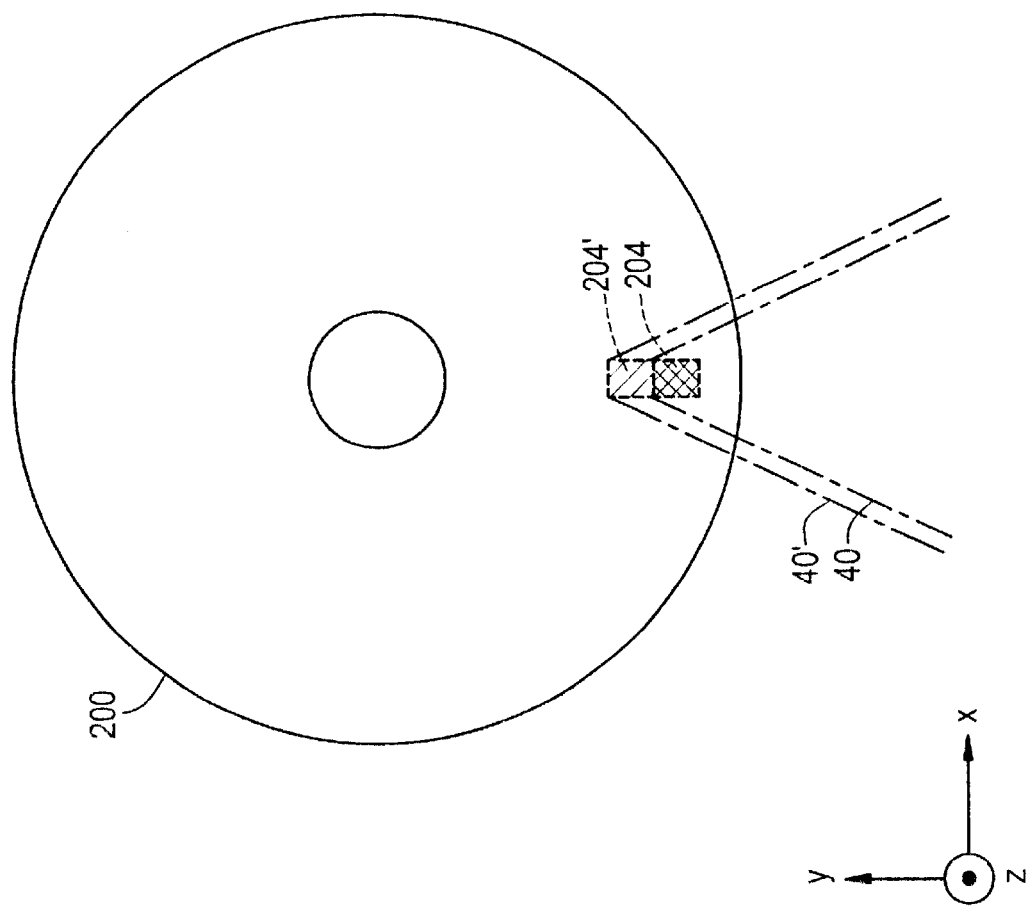

FIG. 9

| Condition | | Axial scan | | | | |
|---|---|---|---|---|---|---|
| | | 1 | 2 | 3 | 4 | 5 |
| Temperature of X-ray tube | (T) | <10% | ← | ← | ← | >90% |
| Tilt angle | (U) | -30° | +30° | ← | ← | ← |
| Scan time | (V) | 3 sec | ← | ← | 0.8 sec | ← |
| Focus size | (W) | small | ← | large | ← | ← |
| Collimator position | | Z1 | Z2 | Z3 | Z4 | Z5 |

FIG. 10

| Condition | | Stationary scan | | | | |
|---|---|---|---|---|---|---|
| | | 1 | 2 | 3 | 4 | 5 |
| Temperature of X-ray tube | (T) | <10% | ← | ← | ← | >90% |
| Tilt angle | (U) | -30° | +30° | ← | ← | ← |
| Scan time | (X) | 0° | ← | ← | 180° | ← |
| Focus size | (W) | small | ← | large | ← | ← |
| Collimator position | | Z1 | Z2 | Z3 | Z4 | Z5 |

X-RAY IMPINGING POSITION ALIGNMENT METHOD AND X-RAY TOMOGRAPHIC IMAGING METHOD AND APPARATUS

BACKGROUND OF THE INVENTION

The present invention relates to an X-ray impinging position alignment method and an X-ray tomographic imaging method and apparatus, and more particularly to an X-ray impinging position alignment method for an X-ray emitting/detecting apparatus that emits an X-ray generated from an X-ray tube onto an X-ray detector through a collimator, and an X-ray tomographic imaging method and apparatus for performing imaging with the X-ray impinging position alignment.

In X-ray CT (computed tomography), an X-ray emitting/detecting apparatus for emitting an X-ray generated from an X-ray tube onto an X-ray detector through a collimator is rotated around (i.e., scans) a subject to be examined, and projection data for the subject is measured using the X-ray in a plurality of view directions around the subject to produce (i.e., reconstruct) a tomographic image based on the projection data.

The X-ray emitting apparatus emits an X-ray beam having a width in which an imaging range is contained and a certain thickness in the direction perpendicular to the width. The thickness of the X-ray beam is determined by the degree of opening of an X-ray passing aperture of the collimator.

The X-ray detecting apparatus detects the X-ray by a multi-channel X-ray detector comprising multiple X-ray detector elements arranged in an array in the direction of the X-ray beam width. The multi-channel X-ray detector has a length (i.e., width) corresponding to the X-ray beam width in the direction of the X-ray beam width, and a length (i.e., thickness) greater than the X-ray beam thickness in the direction of the X-ray beam thickness.

Some X-ray detectors comprise the X-ray detector element array having two rows to simultaneously obtain projection data for two slices. In such X-ray detectors, the two rows of the array are disposed adjacent to each other in parallel, and the X-ray beam impinges upon the detector equally apportioned in the thickness direction. Each thickness of the X-ray beam impinging upon each of the two rows of the array at the subjects isocenter determines the slice thickness of the tomographic image.

In the X-ray tube, an X-ray focus shifts due to thermal expansion caused by a temperature rise during use or the like, resulting in displacement of the X-ray beam in the thickness direction after passing through the collimator aperture. If the X-ray beam is displaced in the thickness direction, the distribution proportion of the X-ray beam thickness between the two rows of the array varies and the respective slice thicknesses for the subject projected on the two series of the array become unequal.

Thus, a technique is employed involving providing the two rows of the array with respective reference channels, monitoring the ratio between X-ray counts at the reference channels, detecting a shift in the X-ray impinging position if the ratio is not equal to one, and adjusting the collimator position, thereby controlling the X-ray impinging position to remain at a fixed position.

However, since the above technique for controlling the impinging position should be started only after the X-ray is emitted and a scan is started, the X-ray impinging position does not always coincide with a fixed position immediately after the beginning of the scan, or rather it may be shifted from the fixed position more often than not. Accordingly, there is a problem that an image initially obtained is subject to quality degradation.

SUMMARY OF THE INVENTION

It is therefore an object of the present invention to provide an X-ray impinging position alignment method to make an X-ray impinging position coincide with a fixed position from the beginning of a scan, and an X-ray tomographic imaging method and apparatus that performs imaging with such X-ray impinging position alignment.

In accordance with a first aspect of the present invention, there is provided an X-ray impinging position alignment method, in performing tomographic imaging by scanning a subject using an X-ray emitting/detecting apparatus for emitting an X-ray generated from an X-ray tube onto an X-ray detector through a collimator, comprising the steps of: predicting an X-ray focus position at the X-ray tube based on the temperature of the X-ray tube prior to beginning the scan and scan conditions intended to be currently used; and adjusting a position of the collimator and/or a position of the X-ray detector according to the predicted position so that the X-ray generated from the X-ray tube impinges upon a fixed position on the X-ray detector.

In accordance with a second aspect of the present invention, there is provided an X-ray tomographic imaging method, in performing tomographic imaging by scanning a subject using an X-ray emitting/detecting apparatus for emitting an X-ray generated from an X-ray tube onto an X-ray detector through a collimator, comprising the steps of: predicting an X-ray focus position at the X-ray tube based on the temperature of the X-ray tube prior to beginning the scan and scan conditions intended to be currently used; adjusting a position of the collimator and/or a position of the X-ray detector according to the predicted position so that the X-ray generated from the X-ray tube impinges upon a fixed position on the X-ray detector; and performing tomographic imaging by scanning the subject using the X-ray emitting/detecting apparatus after being position-adjusted by the adjusting step.

In accordance with a third aspect of the present invention, there is provided an X-ray tomographic imaging apparatus for performing tomographic imaging by scanning a subject using an X-ray emitting/detecting apparatus for emitting an X-ray generated from an X-ray tube onto an X-ray detector through a collimator, comprising: focus position predicting means for predicting an X-ray focus position at the X-ray tube based on the temperature of the X-ray tube prior to beginning the scan and scan conditions intended to be currently used; and position adjusting means for adjusting a position of the collimator and/or a position of the X-ray detector according to the predicted X-ray focus position so that the X-ray generated from the X-ray tube impinges upon a fixed position on the X-ray detector.

In any one of the first through third aspects of the invention, it is preferred that the scan conditions include at least a tilt angle of the X-ray emitting/detecting apparatus and a scan time in that the X-ray focus position can be predicted properly in an axial scan.

In any one of the first through third aspects of the invention, it is preferred that the scan conditions include at least a tilt angle and an azimuth angle of the X-ray emitting/detecting apparatus in that the X-ray focus position can be predicted properly in a stationary scan.

In the above cases, it is preferred that the scan conditions further include an X-ray focus size in that the X-ray focus position can be predicted properly when the X-ray focus size is changed.

The X-ray impinging position alignment method and the X-ray tomographic imaging method and apparatus of the first through third aspects of the present invention can adjust the position(s) of the collimator and/or the X-ray detector according to the X-ray focus position predicted prior to beginning a scan, causing the X-ray to impinge upon a fixed position on the X-ray detector from the very beginning of the scan.

Thus, the present invention can implement an X-ray impinging position alignment method to make an X-ray impinging position coincide with a fixed position from the beginning of a scan, and an X-ray tomographic imaging method and apparatus that performs imaging with such X-ray impinging position alignment.

Further objects and advantages of the present invention will be apparent from the following description of the preferred embodiments of the invention as illustrated in the accompanying drawings.

BRIEF DESCRIPTION OF THE DRAWINGS

FIG. 5 is a schematic showing the X-ray emitting/detecting apparatus in the apparatus shown in FIG. 1.

FIG. 6 is a schematic showing a main portion of an X-ray tube in the apparatus shown in FIG. 1.

FIG. 9 is a diagram showing scan conditions in calibrating the apparatus shown in FIG. 1.

FIG. 10 is a diagram showing scan conditions in calibrating the apparatus shown in FIG. 1.

DETAILED DESCRIPTION OF THE INVENTION

Figure 1:
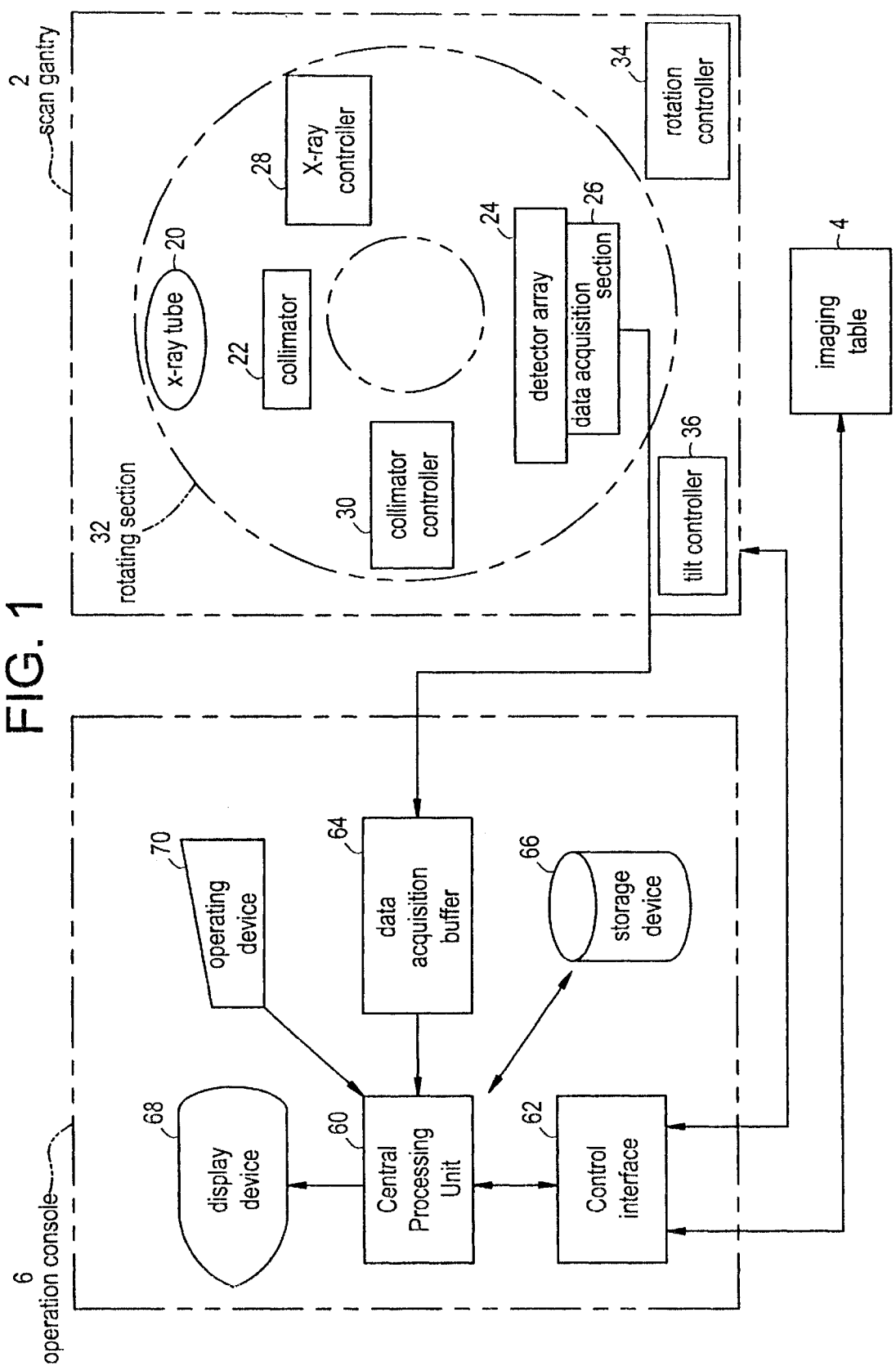
FIG. 1 is a block diagram of an apparatus in accordance with one embodiment of the present invention.

The present invention will now be described in more detail with reference to embodiments shown in the accompanying drawings. FIG. 1 shows a block diagram of an X-ray CT apparatus which is one embodiment of the present invention. The configuration of the apparatus represents an embodiment of the apparatus in accordance with the present invention, and the operation of the apparatus represents an embodiment of the method in accordance with the present invention.

As shown in FIG. 1, the apparatus comprises a scan gantry 2, an imaging table 4 and an operator console 6. The scan gantry 2 has an X-ray tube 20. The X-ray tube 20 represents one embodiment of the X-ray tube in accordance with the present invention. The X-ray tube 20 is provided with a temperature detector (not shown). An X-ray (not shown) emitted from the X-ray tube 20 is formed into, for example, a fan-shaped X-ray beam by a collimator 22 and is made to impinge upon a detector array 24. The collimator 22 represents one embodiment of the collimator in accordance with the present invention. Also, the detector array 24 represents one embodiment of the X-ray detector in accordance with the present invention. The detector array 24 has a plurality of X-ray detector elements arranged in an array in the fan-shaped X-ray beam spreading direction. The configuration of the detector array 24 will be described later.

The X-ray tube 20, the collimator 22 and the detector array 24 together constitute an X-ray emitting/detecting apparatus. The X-ray emitting/detecting apparatus represents one embodiment of the X-ray emitting/detecting apparatus in accordance with the present invention. The configuration of the X-ray emitting/detecting apparatus will be described later. The detector array 24 is connected with a data acquisition section 26 for acquiring data detected by the individual X-ray detector elements in the detector array 24. The data acquisition section 26 also acquires temperature data of the X-ray tube 20.

The emission of the X-ray from the X-ray tube 20 is controlled by an X-ray controller 28. The connection relationship between the X-ray tube 20 and the X-ray controller 28 is omitted in the drawing. The collimator 22 is controlled by a collimator controller 30. The connection relationship between the collimator 22 and the collimator controller 30 is omitted in the drawing.

The above-described components from the X-ray tube 20 through the collimator controller 30 is supported on a rotating section 32 of the scan gantry 2. The rotation of the rotating section 32 is controlled by a rotation controller 34. The connection relationship between the rotating section 32 and the rotation controller 34 is omitted in the drawing. The scan gantry 2 also has a tilt controller 36 for controlling tilt operation of the scan gantry 2.

The imaging table 4 is for carrying a subject (not shown in FIG. 1) into or out of an X-ray irradiation space in the scan gantry 2. The relationship between the subject and the X-ray irradiation space will be described later.

The operator console 6 has a central processing unit 60 that is comprised of, for example, a computer. The central processing unit 60 is connected with a control interface 62, which is in turn connected with the scan gantry 2 and the imaging table 4.

The central processing unit 60 controls the scan gantry 2 and the imaging table 4 via the control interface 62. The data acquisition section 26, the X-ray controller 28, the collimator controller 30, the rotation controller 34 and the tilt controller 36 in the scan gantry 2 are controlled via the control interface 62. The individual connections between these sections and the control interface 62 are omitted in the drawing. The central processing unit 60 represents one embodiment of the focus position predicting means in accordance with the present invention. A section consisting of the central processing unit 60, the control interface 62 and the collimator controller 30 represents one embodiment of the position adjusting means in accordance with the present invention.

The central processing unit 60 is also connected with a data acquisition buffer 64, which is in turn connected with the data acquisition section 26 in the scan gantry 2. Data acquired at the data acquisition section 26 is input to the data acquisition buffer 64 and the buffer 64 temporarily stores the input data.

The central processing unit 60 is also connected with a storage device 66 for storing several data, reconstructed images, programs and the like. The central processing unit 60 is moreover connected with a display device 68 that displays a reconstructed image and other information output from the central processing unit 60, and an operating device 70 that is operated by a human operator to input several commands and information to the central processing unit 60.

Figure 2:
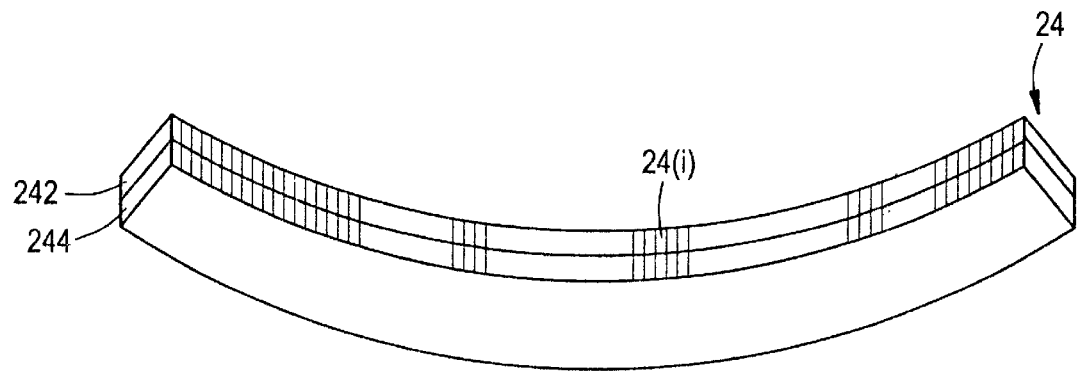
FIG. 2 is a schematic showing a detector array in the apparatus shown in FIG. 1.

FIG. 2 schematically illustrates the configuration of the detector array 24. The detector array 24 is comprised of two rows of multi-channel X-ray detectors 242 and 244 in which a multiplicity (e.g., of the order of 1,000) of X-ray detector elements 24(i) are arranged in an arc shape. Reference symbol 'i' designates a channel index and i=1–1,000; for example. The X-ray detectors 242 and 244 are disposed adjacent to each other in parallel. A certain number of the channels at both ends of the detector array 24 are used as reference channels for each row. The reference channels lie outside of a range within which the subject is projected in imaging.

Figure 3A:
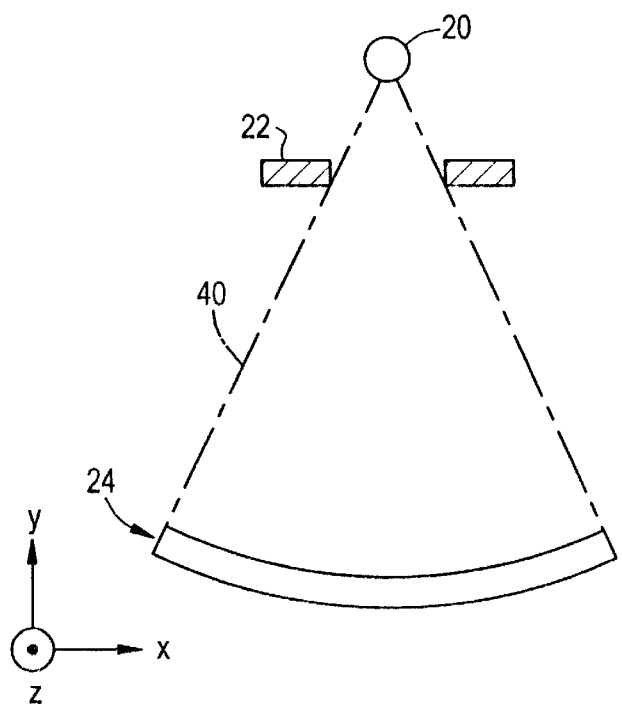
FIG. 3 is a schematic showing an X-ray emitting/detecting apparatus in the apparatus shown in FIG. 1.
Figure 3B:
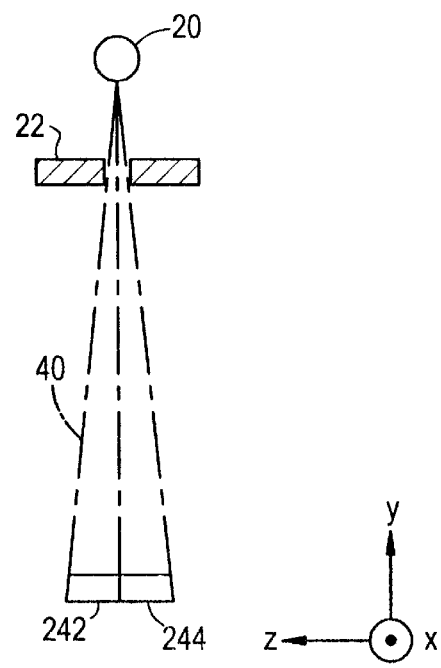

FIG. 3 illustrates the interrelation among the X-ray tube 20, the collimator 22 and the detector array 24 in the X-ray emitting/detecting apparatus. FIG. 3(a) is a front view and (b) is a side view. Three mutually orthogonal coordinate axes in a geometric space formed by the X-ray emitting/detecting apparatus are designated as x, y and z. These symbols are similarly used in the following drawings. As shown in FIG. 3, the X-ray emitted from the X-ray tube 20 is formed into a fan-shaped X-ray beam 40 by the collimator 22 and impinges upon the detector array 24. In FIG. 3(a), the spread of the fan-shaped X-ray beam 40, i.e., the width of the X-ray beam 40 is illustrated. The fan surface of the X-ray beam 40 is parallel to the x-y plane. In FIG. 3(b), the thickness of the X-ray beam 40 is illustrated. The X-ray beam 40 impinges upon the two rows of the X-ray detectors 242 and 244 with its thickness equally apportioned. The thickness direction of the X-ray beam 40 is identical to the z-direction. The z-direction is also identical to the direction of the rotation axis of the X-ray emitting/detecting apparatus.

Figure 4:
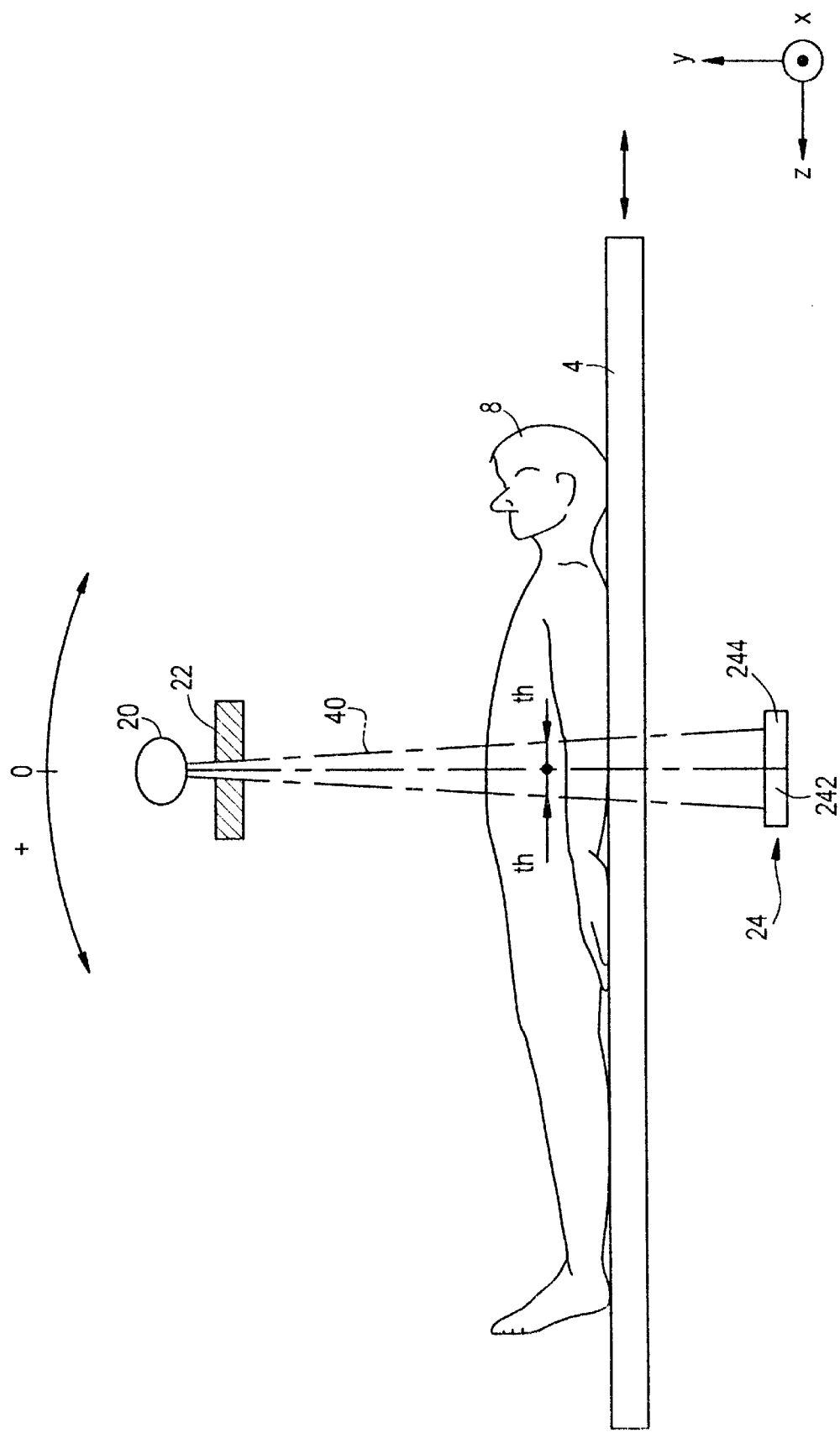
FIG. 4 is a schematic showing the X-ray emitting/detecting apparatus in the apparatus shown in FIG. 1.

As exemplarily shown in FIG. 4, a subject 8 placed on the imaging table 4 is carried into the X-ray irradiation space with the subject's body axis intersecting the fan surface of the X-ray beam 40. The body axis of the subject 8 coincides with the z-direction. A projection image of the subject 8 sliced by the X-ray beam 40 is projected on the detector array 24. A half of the thickness of the X-ray beam 40 at the isocenter of the subject 8 gives each of two slice thicknesses 'th' of the subject 8. The slice thickness 'th' is determined by an aperture of the collimator 22.

A schematic diagram illustrating the impinging state of the X-ray beam on the detector array 24 is shown in FIG. 5 in more detail. As shown, by displacing collimator blocks 220 and 222 in the collimator 22 in the direction such that the aperture is narrowed, the slice thicknesses 'th' of the projection images at the X-ray detector 242 and 244 can be reduced. Similarly, if the collimator blocks 220 and 222 are moved in the direction such that the aperture is widened, the slice thicknesses 'th' of the projection image can be increased. If both of the collimator blocks 220 and 222 defining the slice thicknesses 'th' are simultaneously moved in the z-direction with their relative positional relationship maintained, the impinging z-position on the detector array 24 can be adjusted.

Such slice thickness adjustment and impinging position adjustment are achieved by the collimator controller 30. The impinging z-position is detected based on the output ratio between the respective reference channels of the two rows in the detector array 24, and the position of the collimator 22 is adjusted based on the detected signal so that the slice thicknesses are equalized between the two rows of the detector array. A change of the impinging position with a shift of the focus at the X-ray tube is thus corrected and the X-ray beam 40 is made to constantly impinge upon a fixed position. This function is referred to as an autocollimator hereinbelow.

It should be noted that the impinging z-position may be adjusted by displacing the detector array 24 in the z-direction relative to the collimator 22 as indicated by broken arrow in FIG. 5, instead of moving the collimator blocks 220 and 222. Thus, two mechanisms for adjusting the slice thickness and for controlling the impinging position in the thickness direction can be separated, thereby allowing diversification of control. On the other hand, if the entire control is carried out only by the collimator 22 as described hereinbefore, the control mechanisms can be integrated all in one, thereby satisfying the need to simplify configuration. It will be easily recognized that these two means may be combined to achieve the impinging position adjustment.

The X-ray emitting/detecting apparatus consisting of the X-ray tube 20, the collimator 22 and the detector array 24 rotates around the body axis of the subject 8 (i.e., an axial scan) with their interrelation maintained. Projection data for the subject are acquired at a plurality (e.g., of the order of 1,000) of view angles per scan rotation. The acquisition of the projection data is performed by a line consisting of the detector array 24, the data acquisition section 26 and the data acquisition buffer 64.

Based on the projection data for two slices collected in the data acquisition buffer 64, the central processing unit 60 produces tomographic images, i.e., performs image reconstruction, for the two slices. The image reconstruction is carried out by processing the projection data for, for example, 1,000 views obtained from a scan during one rotation using, for example, a filtered backprojection technique.

If the scan gantry 2 is tilted by the tilt controller 36, the rotation axis of the X-ray emitting/detecting apparatus (i.e., z-axis) is inclined with respected to the body axis of the subject 8. This allows scanning of a slice plane slanted counterclockwise or clockwise in the drawing of FIG. 4.

Moreover, a penetration image of the subject 8 is captured by emitting an X-ray with the rotation of the X-ray emitting/detecting apparatus stopped and acquiring projection data while moving the imaging table 4 in the direction of the body axis of the subject 8. Such penetration imaging is sometimes referred to as a stationary scan. The penetration image may be obtained as a front image, a side image or an oblique side image at any arbitrary angle, corresponding to the position of the X-ray tube 20 on the rotation orbit The position of the X-ray tube 20 on the rotation orbit in the penetration imaging is indicated by an angle (i.e., an azimuth) relative to the y-direction.

FIG. 6 schematically shows the configuration of a main portion of the X-ray tube 20, in which (a) is a front view and (b) is a side view. As shown, a rotary anode 200 and a cathode 202 are provided facing each other within an evacuated tube (not shown). Between the rotary anode 200 and the cathode 202 is applied a predetermined high voltage. The rotary anode 200 is driven by a drive section (not shown) to rotate at a high speed. The rotary anode 200 hasaslope surface facing the cathode 202 onto which an electron beam is emitted from the cathode 202 to generate the X-ray beam 40 by collision energy of the electron beam.

The electron beam impinging area on the surface of the rotary anode 200 can be switched between two areas, i.e., a small area 204 and a large are 204', by switching the cathode 202, for example. The small area 204 forms a small X-ray focus for generating the X-ray beam 40, and the large area 204' forms a large X-ray focus for generating the X-ray beam 40'. The X-ray focus will be referred to simply as a focus hereinafter.

The collision energy of the electron beam raises the temperature of the rotary anode 200, and hence the temperature of the X-ray tube 20. The temperature of the X-ray tube 20 rises corresponding to the duration time of the X-ray irradiation. The temperature rise is accompanied with thermal expansion that causes the focus z-position to be displaced. The direction of the displacement is identical to the direction in which the rotation axis of the rotary anode 200 extends, which will be designated as "+(plus)-direction" and the opposite direction as "–(minus)-direction".

Although the absolute amount of the displacement is small, since the displacement is magnified by optical leverage with a fulcrum of the collimator aperture, it appears as a significant shift distance on the X-ray impinging surface of the detector array 24. The same applies to the focus shift due to other factors as described below.

The focus z-shift is also resulted from the tilt of the scan gantry 2. Specifically, if the scan gantry 2 is tilted counter-clockwise in FIG. 4 (i.e., in the (+)-direction) the focus is displaced in the (+)-direction, for example, and if the scan gantry 2 is tilted clockwise (i.e., in the (–)-direction) the focus is displaced in the (–)-direction, for example. Moreover, the focus z-position is affected by the rotation speed of the scan gantry 2 during a scan. Specifically, since a centrifugal force due to the rotation of the scan gantry 2 acts on the X-ray tube 20 and the force varies according to the rotation speed, the focus shifts in the (+)-direction, for example, as the rotation speed becomes high, i.e., the scan time becomes short.

Furthermore, when the focus is switched between the large one and the small one by varying the electron beam impinging area on the rotary anode 200 as shown in FIG. 6, the focus z-position shifts because of the slope of the electron beam impinging surface of the rotary anode 200. In addition, when the stationary scan is performed, the focus z-position is affected by the azimuth of the X-ray tube 20, although not by the scan time. Specifically, when the azimuth is 0° the maximum displacement occurs in the (+)-direction, for example, and when the azimuth is 180° the maximum displacement occurs in the (–)-direction, for example. Similarly, an azimuth between 0° and 180° results in an intermediate displacement.

The focus z-position is thus varied by the factors consisting of at least the temperature of the X-ray tube 20, the tilt angle of the scan gantry 2, the scan time, the focus size (large or small), and the azimuth. Therefore, the central processing unit 60 predicts the focus shift based on these factors at the beginning of a scan, and calculates the z-offset distance of the collimator 22 to make the impinging position of the X-ray beam 40 coincide with a fixed position on the detector array 24. Alternatively, if a mechanism for adjusting the position of the detector array 24 is provided, the z-offset distance of the detector array 24 may be calculated to make the impinging position of the X-ray beam 40 coincide with the fixed position on the detector array 24. The position of the collimator 22 (and/or the position of the detector array 24) is then adjusted according to the calculated value, and the scan is started.

Figure 7:
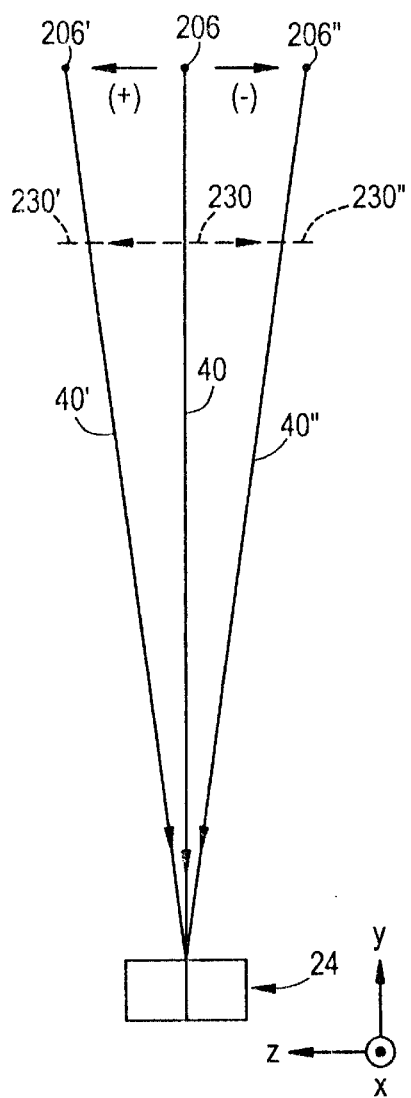
FIG. 7 is a schematic showing focus shift at the X-ray tube and its corresponding position adjustment of the collimator in the apparatus shown in FIG. 1.

FIG. 7 shows a diagram representing the concept of the focus shift and its corresponding position adjustment of the collimator. Referring to FIG. 7, a standard state is defined as the state when the focus lies at a position 206 on a normal line extending from the z-center of the detector array 24, and a standard collimator position is defined as a position 230 of the collimator 22 through which the X-ray beam 40 impinges upon the center of the detector array 24 in the standard state.

When the focus shifts from the standard state to a position 206' in the left (+) direction in the drawing, in order to make the X-ray beam 40' that emanates therefrom impinge upon the center of the detector array 24, the collimator 22 must be offset from the standard position 230 to a position 230' in the (+)-direction. Similarly, when the focus shifts from the standard state to a position 206" in the right (–) direction in the drawing, in order to make the X-ray beam 40" that emanates therefrom impinge upon the center of the detector array 24, the collimator 22 must be offset from the standard position 230 to a position 230" in the (–)-direction. The offset distance Z of the collimator 22 is proportional to the focus shift distance z, as given by the following equation:

$$Z = G1 \cdot z, \quad (1)$$

wherein the proportion constant G1 (gain) is a positive value less than 1.

Figure 8:
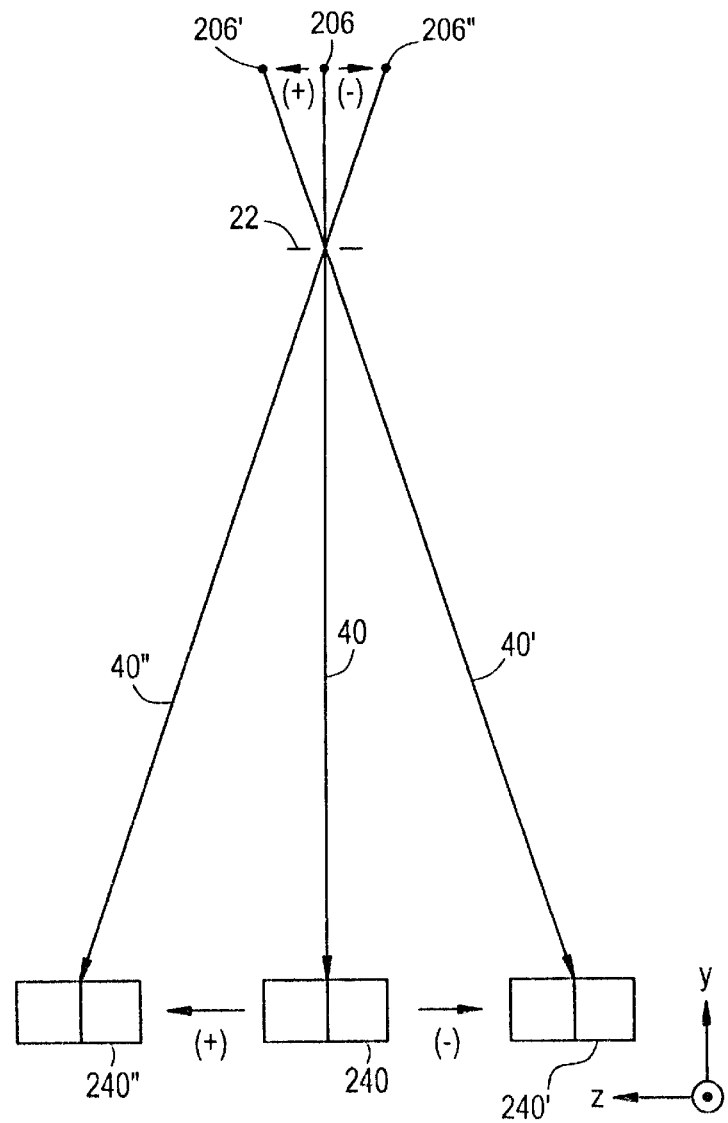
FIG. 8 is a schematic showing focus shift at the X-ray tube and its corresponding position adjustment of the detector array in the apparatus shown in FIG. 1.

FIG. 8 shows a diagram representing the concept of the focus shift and its corresponding position adjustment of the detector array. When the focus shifts from the standard state to a position 206' in the left (+) direction in the drawing, in order to make the X-ray beam 40' that emanates therefrom impinge upon the center of the detector array 24, the detector array 24 must be offset from the standard position 240 to a position 240' in the (–)-direction. Similarly, when the focus shifts from the standard state to a position 206' in the right (–) direction in the drawing, in order to make the X-ray beam 40 that emanates therefrom impinge upon the center of the detector array 24, the detector array 24 must be offset from the standard position 240 to a position 240" in the (+)-direction. The offset distance Z of the detector array 24 is proportional to the focus shift distance z, as given by the following equation:

$$Z = G2 \cdot z, \quad (2)$$

wherein the proportion constant G2 (gain) is a negative value whose absolute value is greater than 1.

The inventors discovered that in the axial scan, the focus shift distance and the aforementioned factors have a relationship as follows:

$$z = k + a\left\{\frac{2}{T_1 - T_2}(T - T_2) - 1\right\} + b\left\{\frac{2}{U_1 - (-U_2)}(U + U_2) - 1\right\} - c\left\{\frac{2}{V_1 - V_2}(V - V_2) - 1\right\} + d(2W + 1), \quad (3)$$

wherein,

T: the temperature of the X-ray tube in percentage to the operating temperature range, T1: the upper limit of the temperature range, for example, 90%, T2: the lower limit of the temperature range, for example, 10%, U: the tilt angle U1: the upper limit of the tilt angle in the (+)-direction, for example, 30°, U2: the upper limit of the tilt angle in the (–)-direction, for example, 30°, V: the scan time, V1: the longest scan time, for example, 3 seconds, V2: the shortest scan time, for example, 0.8 seconds, W: the focus size, 'large'=1 and 'small'=0, and a, b, c, d, k: constants.

The inventors also discovered that in the stationary scan, the focus shift distance and the aforementioned factors have a relationship as follows:

$$z = k' + a'\left\{\frac{2}{T_1 - T_2}(T - T_2) - 1\right\} + b'\left\{\frac{2}{U_1 - (-U_2)}(U + U_2) - 1\right\} - c'\left\{\frac{2}{180 - 0}(X - 0) - 1\right\} + d'(2W + 1), \quad (4)$$

wherein,

T: the temperature of the X-ray tube in percentage to the operating temperature range, T1: the upper limit of the temperature range, for example, 90%, T2: the lower limit of the temperature range, for example, 10%, U: the tilt angle U1: the upper limit of the tilt angle in the (+)-direction, for example, 30°, U2: the upper limit of the tilt angle in the (−)-direction, for example, 30°, X: the azimuth, W: the focus size, 'large'=1 and 'small'=0, and a', b', c', d', k': constants.

The central processing unit 60 predicts the focus shift distance z according to Eq. (3) in the axial scan and according to Eq. (4) in the stationary scan, calculates the distance Z over which the collimator 22 is to be moved, according to Eq. (1) using the predicted value, and performs position adjustment via the collimator controller 30 based on the calculated distance Z. It should be noted that the distance Z is calculated according to Eq. (2) when the position of the detector array 24 is to be adjusted.

However, since Eq. (1) represents the case in which the initial position of the collimator 22 coincides with the standard position, the offset distance Z' of the collimator 22 is generally calculated using Eq. (5) given below that contains a shift z0 of the current position of the collimator 22 from the standard position. It should be noted that the current position of the collimator 22 is always monitored by the central processing unit 60. The same applies to the case in which the position of the detector array 24 is to be adjusted.

$$Z' = G1 \cdot z - z0. \quad (5)$$

The inventors further found equations for directly calculating the offset distance of the collimator 22 based on the aforementioned factors, as given below. Although not being specifically discriminated in the equations below, it is obvious that the prediction of the focus shift is involved.

With respect to the axial scan, $$Z' = AT + BU + CV + DW - K - z0, \quad (6)$$

wherein,

A, B, C, D, K: constants.

With respect to the stationary scan, $$Z' = AT + BU + CX + DW - K - z0, \quad (7)$$

wherein,

A, B, C, D, K: constants.

The constants A–K can be obtained by calibrating the present apparatus. The calibration is performed by scans with the scan conditions differentiated one by one. It will be easily recognized that the calibrating scans are carried out without supporting the subject 8.

The order of the scans and their respective conditions for the axial scan are exemplarily shown in a table in FIG. 9. First, the collimator 22 is aligned with the standard position and a first scan 1 is performed in this state. As shown in the table, the scan conditions are as follows: the temperature of the X-ray tube is below 10% of the operating temperature range, the tilt angle is −30°, the scan time is 3 seconds, and the focus size is 'small'. The scan is carried out with the autocollimator function. Thus, the position of the collimator 22 is automatically adjusted so that the impinging position of the X-ray beam 40 is at a fixed position. Then a collimator position Z1 after being automatically adjusted is obtained. Z1 reflects a focus position affected by the scan conditions for the scan 1.

Next, a scan 2 is performed. The scan conditions are the same as those in the scan 1 except that the tilt angle is +30°. From this scan, a position Z2 of the collimator 22 after being automatically adjusted by the autocollimator is obtained. Z2 reflects a focus position affected by the scan conditions for the scan 2 and differs from Z1 only in the effect of the tilt angle.

Next, a scan 3 is performed. The scan conditions are the same as those in the scan 2 except that the focus size is 'large'. From this scan, a position Z3 of the collimator 22 after being automatically adjusted by the autocollimator is obtained. Z3 reflects a focus position affected by the scan conditions for the scan 3 and differs from Z2 only in the effect of the focus size.

Next, a scan 4 is performed. The scan conditions are the same as those in the scan 3 except that the scan time is 0.8 seconds. From this scan, a position Z4 of the collimator 22 after being automatically adjusted by the autocollimator is obtained. Z4 reflects a focus position affected by the scan conditions for the scan 4 and differs from Z3 only in the effect of the scan time.

After these scans, an idle scan is continuously performed to raise the temperature of the X-ray tube. During the idle scan, the autocollimator function is not employed. When the temperature of the X-ray tube reaches more than 90% of the operating temperature range, a scan 5 is performed. The scan conditions are the same as those in the scan 4 except that the temperature of the X-ray tube is greater than 90% of the operating temperature range. From this scan, a position Z5 of the collimator 22 after being automatically adjusted by the autocollimator is obtained. Z5 reflects a focus position affected by the scan conditions for the scan 5 and differs from Z4 only in the effect of the temperature of the X-ray tube 20.

The data Z1–Z5 thus obtained are used to calculate the constants A–K according to the equation as follows:

$$A = \frac{Z5 - Z4}{T_1 - T_2}, \quad (8)$$

$$B = \frac{Z2 - Z1}{U_1 - (-U_2)},$$

$$C = \frac{Z4 - Z3}{V_2 - V_1},$$

D = Z3−Z2, and

K = Z1, wherein T1, T2, U1, U2, V1 and V2 are the same as those in Eq. (3).

The order of the scans and their respective conditions for the stationary scan are exemplarily shown in a table in FIG. 10. First, the collimator 22 is aligned with the standard position and a first scan 1 is performed in this state. As shown in the table, the scan conditions are as follows: the temperature of the X-ray tube is below 10% of the operating temperature range, the tilt angle is −30°, the azimuth is 0°, and the focus size is 'small'. The scan is carried out with the autocollimator function. Thus, the position of the collimator 22 is automatically adjusted so that the impinging position of the X-ray beam 40 is at a fixed position. Then a collimator position Z1 after being automatically adjusted is obtained.

Next, a scan 2 is performed. The scan conditions are the same as those in the scan 1 except that the tilt angle is +30°. From this scan, a position Z2 of the collimator 22 after being automatically adjusted by the autocollimator is obtained.

Next, a scan 3 is performed. The scan conditions are the same as those in the scan 2 except that the focus size is 'large'. From this scan, a position Z3 of the collimator 22 after being automatically adjusted by the autocollimator is obtained.

Next, a scan 4 is performed. The scan conditions are the same as those in the scan 3 except that the azimuth is 180°. From this scan, a position Z4 of the collimator 22 after being automatically adjusted by the autocollimator is obtained.

After these scans, the X-ray irradiation is continuously performed to raise the temperature of the X-ray tube. During this time, the autocollimator function is not employed. When the temperature of the X-ray tube reaches more than 90% of the operating temperature range, a scan 5 is performed. The scan conditions are the same as those in the scan 4 except that the temperature of the X-ray tube is greater than 90% of the operating temperature range. From this scan, a position Z5 of the collimator 22 after being automatically adjusted by the autocollimator is obtained.

The data Z1–Z5 thus obtained are used to calculate the constants A–K according to the equation as follows:

$$A = \frac{Z5 - Z4}{T_1 - T_2}, \tag{9}$$

$$B = \frac{Z2 - Z1}{U_1 - (-U_2)},$$

$$C = \frac{Z4 - Z3}{0 - 180},$$

D=Z3−Z2, and

K=Z1, wherein T1, T2, U1, and U2 are the same as those in Eq. (4).

Eqs. (5), (6) and (7) each represent the case in which the X-ray beam 40 is emitted so that the slice thicknesses at the two detector rows are equalized, but if the slice thickness ratio of the two detector rows is generally 1:n (n≧1), a correction can be made for displacing the position of the collimator 22 to the side having a greater slice thickness ratio by a distance 'zn' given as follows:

$$zn = \left(n - \frac{1+n}{2}\right)\frac{M}{1+n}, \tag{10}$$

wherein,

M: the total width of the collimator aperture.

Now the operation of the present apparatus will be described. The operation of the apparatus proceeds under control of the central processing unit 60 based on commands issued by a human operator. The operator inputs the imaging conditions via the operating device 70. The imaging conditions include the tube voltage, the tube current, the slice thickness, the slice position, the tilt angle, the scan time, the focus size, and the like. In the stationary scan, the azimuth is included instead of the scan time. Although description will be made with reference to the axial scan hereinafter, the same applies to the stationary scan. Moreover, although description will be made with reference to the case in which the position of the collimator 22 is adjusted, the same applies to the case of adjusting the position of the detector array 24 or the case of adjusting the positions of the collimator 22 and the detector array 24.

The central processing unit 60 predicts the focus z-position of the X-ray tube 20 at the beginning of a scan from the scan conditions and the temperature measurement of the X-ray tube 20 based on Eq. (3), and calculates the z-position Z' of the collimator 22 from Eq. (5). Alternatively, the z-position Z' of the collimator 22 is directly calculated based on Eq.(6).

Next, based on a command issued by the operator, the imaging table 4 supporting the subject 8 is positioned and subsequently the rotating section 32 of the scan gantry 2 is rotated and an X-ray is emitted to start an axial scan. Since the z-positon Z' of the collimator 22 has been adjusted corresponding to the focus position z of the X-ray tube 20 at the beginning of the scan, the X-ray beam 40 impinges upon a fixed position on the detector array 24 from the beginning of the scan. In addition, with respect to the focus shift due to a temperature rise of the X-ray tube that occurs from the beginning of the scan, the impinging position is stabilized by the autocollimator function.

The central processing unit 60 performs image reconstruction based on view data acquired during the scan. The image reconstruction is performed by processing the view data by a technique such as filtered backprojection. A tomographic image of the subject 8 is obtained by the image reconstruction. Since the X-ray impinges upon a fixed position on the detector array 24 from the beginning, the reconstructed image can be obtained with a good quality from the beginning.

Since the detector array 24 has two parallel rows of X-ray detectors, tomographic images for two adjacent slices can be simultaneously obtained in one scan. This improves efficiency in performing a multi-slice scan or a helical scan. The reconstructed image is displayed on the display device 68 and also is stored in the storage device 66.

Thus, prior to beginning a scan, the focus position at the X-ray tube 20 is predicted and the initial position of the collimator 22 etc. is adjusted so that the X-ray beam 40 impinges upon a fixed position on the detector array. It is preferred that such position adjustment be performed whenever the scan dwell time exceeds one hour, for example, in order to obtain an image with a good quality. Even when the dwell time does not exceed one hour, the position adjustment should be performed if the temperature of the X-ray tube falls below 10% of the operating temperature range.

Moreover, in other cases, it is recommended that the position adjustment be performed when the difference between a predicted offset amount obtained from the scan conditions intended to be currently used and a predicted offset amount obtained from the scan conditions previously used exceeds a certain limit. Furthermore, it is preferred that the position adjustment be performed each time imaging series or examination is changed in order to obtain an image always with a good quality.

Although reference is made to a detector array consisting of two rows of X-ray detectors in the preceding description, it may consist of multiple rows, i.e., three or more rows, or obviously it may be a single-row detector array.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray impinging position alignment method used perform tomographic imaging by scanning a subject positioned on a gantry using an X-ray emitting/detecting apparatus which emits an X-ray beam generated by an X-ray tube onto an X-ray detector through a collimator, said method comprising the steps of:

obtaining at least two of the following: temperature of said X-ray tube, tilt angle of said gantry, scan time, focus size of said X-ray beam, and azimuth of said X-ray beam;

calculating an X-ray focus shift at said X-ray tube based on said at least two of said temperature, tilt angle, scan time, focus size and azimuth; and providing an offset distance of said collimator and/or said X-ray detector according to said calculated shift so that said X-ray beam coincides with a predetermined position on said X-ray detector.

2. An X-ray tomographic imaging method used to perform tomographic imaging by scanning a subject positioned on a gantry using an X-ray emitter/detector apparatus which emits an X-ray beam generated by an X-ray tube onto an X-ray detector through a collimator, said method comprising the steps of:

obtaining at least two of the following: temperature of said X-ray tube, tilt angle of said gantry, scan time, focus size of said X-ray beam, and azimuth of said X-ray beam;

calculating an X-ray focus shift at said X-ray tube based on said at least -two of said temperature, tilt angle, scan time, focus size and azimuth;

providing an offset distance of said collimator and/or said X-ray detector according to said calculated shift;

adjusting position of said collimator and/or said X-ray detector using said offset distance so that said X-ray beam impinges on a predetermined position on said X-ray detector; and performing tomographic imaging by scanning said subject using said X-ray emitter/detector apparatus after said collimator and/or said X-ray detector is position adjusted in the foregoing step.

3. An X-ray tomographic imaging apparatus for performing tomographic imaging by scanning a subject positioned on a gantry using an X-ray emitter/detector apparatus which emits an X-ray beam generated by an X-ray tube onto an X-ray detector through a collimator, said apparatus comprising:

means for obtaining at least two of the following: temperature of said X-ray tube, tilt angle of said gantry, scan time, focus size of said X-ray beam, and azimuth of said X-ray beam;

means for calculating an X-ray focus shift at said X-ray tube based on said at least two of said temperature, tilt angle, scan time, focus size and azimuth;

means for providing an offset distance of said collimator and/or said X-ray detector based on said shift calculated in the prior step; and means for adjusting position of said collimator and/or said X-ray detector according to said offset distance so that said X-ray impinges on a predetermined position on said X-ray detector.

4. The method of claim 1, wherein said obtaining step obtains three or more of the following: temperature of said X-ray tube, tilt angle of said gantry, scan time, focus size of said X-ray beam, and azimuth of said X-ray beam; and wherein said calculating step calculates an X-ray focus shift at said X-ray tube based on said three or more of said temperature, tilt angle, scan time, focus size and azimuth.

5. The method of claim 2, wherein said obtaining step obtains three or more of the following: temperature of said X-ray tube, tilt angle of said gantry, scan time, focus size of said X-ray beam, and azimuth of said X-ray beam; and wherein said calculating step calculates an X-ray focus shift at said X-ray tube based on said three or more of said temperature, tilt angle, scan time, focus size and azimuth.

6. The apparatus of claim 3, wherein said means for obtaining obtains three or more of the following: temperature of said X-ray tube, tilt angle of said gantry, scan time, focus size of said X-ray beam, and azimuth of said X-ray beam; and wherein said means for calculating calculates an X-ray focus shift at said X-ray tube based on said three or more of said temperature, tilt angle, scan time, focus size and azimuth.

* * * * *